United States Patent
Lee et al.

(10) Patent No.: US 11,832,955 B2
(45) Date of Patent: Dec. 5, 2023

(54) METHOD AND APPARATUS FOR PROVIDING INFORMATION NEEDED FOR DEMENTIA DIAGNOSIS

(71) Applicant: NEUROPHET Inc., Seoul (KR)

(72) Inventors: Ji Yeon Lee, Seoul (KR); Dong Hyeon Kim, Namyangju-si (KR); Min Ho Lee, Seoul (KR); Eun Young Kim, Gwacheon-si (KR)

(73) Assignee: NEUROPHET Inc., Seoul (KR)

( * ) Notice: Subject to any disclaimer, the term of this patent is extended or adjusted under 35 U.S.C. 154(b) by 0 days.

(21) Appl. No.: 18/054,068

(22) Filed: Nov. 9, 2022

(65) Prior Publication Data

US 2023/0263457 A1 Aug. 24, 2023

(30) Foreign Application Priority Data

Feb. 22, 2022 (KR) .......................... 10-2022-0023102

(51) Int. Cl.
G06K 9/00 (2022.01)
A61B 5/00 (2006.01)
(Continued)

(52) U.S. Cl.
CPC .......... *A61B 5/4088* (2013.01); *A61B 5/0035* (2013.01); *A61B 5/7267* (2013.01); (Continued)

(58) Field of Classification Search
None
See application file for complete search history.

(56) References Cited

U.S. PATENT DOCUMENTS

2015/0080703 A1  3/2015  Reiman

FOREIGN PATENT DOCUMENTS

EP        3851036 A1        7/2021
KR   10-2019-0041136 A     4/2019
(Continued)

OTHER PUBLICATIONS

Mathotaarachchi ("Identifying incipient dementia individuals using machine learning and amyloid imaging", Neurobology of Aging, Nov. 2017, vol. 59, p. 80-90) (Year: 2017).*

(Continued)

*Primary Examiner* — Wei Wen Yang
(74) *Attorney, Agent, or Firm* — BROADVIEW IP LAW, PC

(57) ABSTRACT

Preferred embodiments of the present invention provide an apparatus and method for providing information needed for dementia diagnosis. In the apparatus and method in accordance with preferred embodiments of the present invention, an MRI brain image and a PET brain image of a subject for diagnosis are received, the MRI brain image is divided into a plurality of regions, and then the MRI brain image is registered with the PET brain image. Then, a standardized uptake value ratio of each divided region is obtained from the registered image, and for each divided region, a standard value indicating the degree of proximity of a standardized uptake value ratio of the subject for diagnosis to the average value of the standardized uptake value ratios of the group of the Alzheimer's patients and the average value of the standardized uptake value ratios of the normal group, which are stored in advance, is obtained.

11 Claims, 7 Drawing Sheets

(51) Int. Cl.
G06T 7/11 (2017.01)
G06T 7/33 (2017.01)
G16H 30/40 (2018.01)
G16H 50/70 (2018.01)
G16H 50/20 (2018.01)

(52) U.S. Cl.
CPC ............... G06T 7/11 (2017.01); G06T 7/337 (2017.01); G16H 30/40 (2018.01); G16H 50/20 (2018.01); G16H 50/70 (2018.01); *G06T 2207/10088* (2013.01); *G06T 2207/10104* (2013.01); *G06T 2207/20081* (2013.01); *G06T 2207/30016* (2013.01)

(56) References Cited

FOREIGN PATENT DOCUMENTS

| KR | 20190132832 A | * | 11/2019 |
| KR | 10-2022-0016570 A | | 2/2022 |
| WO | 2017/048904 A1 | | 3/2017 |
| WO | WO-2020218460 A1 | * | 10/2020 |

OTHER PUBLICATIONS

Jo, Taeho et al. "Deep Learning in Alzheimer's Disease: Diagnostic Classification and Prognostic Prediction Using Neuroimaging Data." Article. Department of Radiology and Imaging Sciences, Center for Neuroimaging, Indiana University School of Medicine. Aug. 20, 2019.
Extended European Search Report for EP 22206526.0 by European Patent Office dated Jul. 5, 2023.

* cited by examiner

FIG. 2

| ALZHEIMER'S GROUP | | | | | NORMAL GROUP | | | | |
|---|---|---|---|---|---|---|---|---|---|
| | $R_1$ | $R_2$ | ... | $R_N$ | | $R_1$ | $R_2$ | ... | $R_N$ |
| $A_1$ | $V_{A1R1}$ | $V_{A1R2}$ | | $V_{A1RN}$ | $B_1$ | $V_{B1R1}$ | $V_{B1R2}$ | | $V_{B1RN}$ |
| $A_2$ | $V_{A2R1}$ | $V_{A2R2}$ | | $V_{A2RN}$ | $B_2$ | $V_{B2R1}$ | $V_{B2R2}$ | | $V_{B2RN}$ |
| . | . | . | | . | . | . | . | | . |
| . | . | . | | . | . | . | . | | . |
| $A_M$ | $V_{AMR1}$ | $V_{AMR2}$ | | $V_{AMRN}$ | $B_M$ | $V_{BMR1}$ | $V_{BMR2}$ | | $V_{BMRN}$ |
| AVERAGE | $AV_{AR1}$ | $AV_{AR2}$ | | $AV_{ARN}$ | AVERAGE | $AV_{BR1}$ | $AV_{BR2}$ | | $AV_{BRN}$ |

FIG. 4
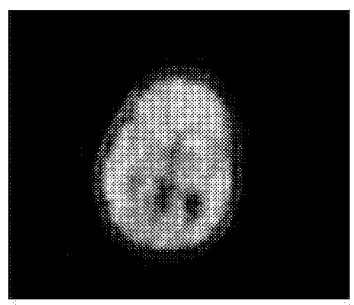
(a)
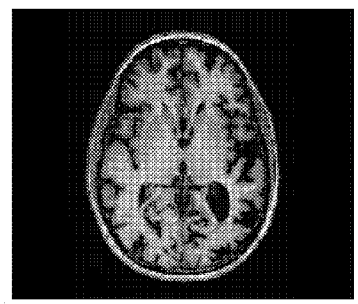
(b)
FIG. 5
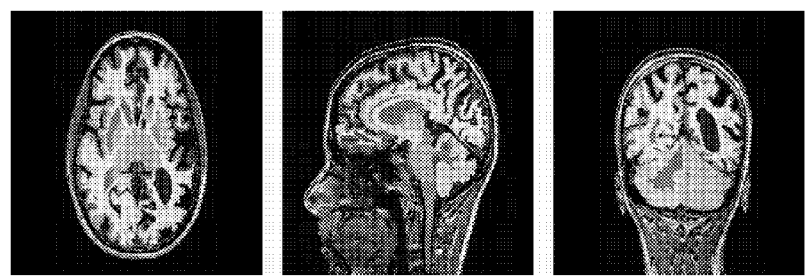

METHOD AND APPARATUS FOR PROVIDING INFORMATION NEEDED FOR DEMENTIA DIAGNOSIS

CROSS-REFERENCE TO RELATED APPLICATIONS

This U.S. non-provisional patent application claims priority under 35 U.S.C. § 119 of Korean Patent Application No. 10-2022-0023102, filed on, Feb. 22, 2022, the entire contents of which are hereby incorporated by reference.

FIELD OF THE INVENTION

The present invention disclosed herein relates to a method and apparatus for providing information needed for dementia diagnosis, and more particularly, to an apparatus and method for providing useful information for dementia diagnosis by acquiring a standardized uptake value ratio for a brain image of a subject for diagnosis.

BACKGROUND ART

Dementia refers to a clinical syndrome in which the cognitive functions of various regions, such as memory, language, and judgment, are reduced and daily life is unable to be properly performed. A typical dementia is senile dementia called Alzheimer's disease, and vascular dementia caused by stroke, and in addition, there is dementia due to various causes, but 50% to 70% of dementia patients are dementia due to Alzheimer's disease.

Alzheimer's disease develops long before symptoms appear, but changes in the brain are not easily noticed until symptoms appear. The time when conspicuous symptoms such as memory loss and language disorder appear is after some degree of brain change has already occurred. The symptoms are due to damage or destruction of nerve cells in the brain involved in thinking, learning, and memory (cognitive function). As the disease progresses, other neurons in the brain are damaged and destroyed, eventually affecting basic physical activities such as walking and swallowing food. Therefore, prompt and accurate diagnosis of Alzheimer's disease is very important.

As a method for diagnosing Alzheimer's disease and the resulting Alzheimer's dementia, there is a diagnostic method by an amyloid positron emission tomography (PET) image. PET stands for positron emission tomography, and refers to a method of injecting a test drug that emits radiation into a patient, and detecting the radiation emitted by the drug from the outside to photograph the inside of the body. As the test drug, a compound is used that is easily attached to amyloid beta, and by administering the compound, only amyloid beta may be labeled. As a result, it is possible to check how much amyloid beta is accumulated in which part of the brain by using the image and analyze the accumulated area and amount for use to differentiate Alzheimer's disease patients.

A typical diagnostic method using amyloid PET is a method using amyloid standardized uptake value ratio (SUVR). Amyloid standardized uptake value ratio (SUVR) represents a ratio of amyloid standardized uptake value (SUV) from two different regions within the same amyloid PET image (target and reference region), and the amyloid standardized uptake value (SUV) may represent the ratio of the concentration of radioactivity of the image to the concentration of radioactivity of the whole injected body.

The amyloid standardized uptake value ratio (SUVR) is being used as the main data for determining the progression of Alzheimer's disease. For example, the Alzheimer's Disease Neuroimaging Initiative (ADNI), an organization that collects data such as PET images and cognitive tests and conducts research by validating and utilizing the data, suggests an SUVR value of approximately 1.10 based on a florbetapir tracer, as a criterion for quantitatively classifying beta amyloid positive and negative. In this case, the value of 1.10 represents the confidence limit value for the top 5% of the distribution of the amyloid standardized uptake value ratio (SUVR) obtained from a control group of 21 people under the age of 55 years. That is, the ADNI suggests determining whether amyloid is positive or negative based on 1.10 of the amyloid standardized uptake value ratio (SUVR) through the analysis of amyloid PET images.

However, as a diagnosis result using amyloid PET images in the related art, only determination may be made as to whether amyloid is positive or negative, and there is a limitation in not providing additional information for determining whether dementia is positive or negative. In addition, when the standardized uptake value ratio is distributed around a threshold value of the amyloid positive or negative determination, there is a limitation in not providing more useful information to doctors who diagnose dementia.

SUMMARY OF THE INVENTION

In order to solve the problem described above, the present invention provides an apparatus and method for providing information needed for dementia diagnosis, capable of providing various useful information for dementia diagnosis to medical staff performing dementia diagnosis by using a PET images, in addition to simply providing a standardized uptake value ratio (SUVR), by providing a weighted standardized uptake value ratio indicating the degree to which the standardized uptake value ratio (SUVR) of the subject is close to the average value of the normal group and the average value of the Alzheimer's group.

In accordance with a preferred embodiment of the present invention in order to solve the aforementioned problems, disclosed is a method for providing information needed for dementia diagnosis that is performed in an apparatus for providing information needed for dementia diagnosis, the apparatus including a processor and a memory for storing predetermined instructions, the method including: (a) calculating a standardized uptake value ratio (SUVR) for each of regions (divided regions) obtained by dividing a brain region of a brain image of a subject for diagnosis into a plurality of predefined regions; (b) obtaining a standard value by mapping the standardized uptake value ratio of each divided region to a standard interval defined in advance for each divided region; (c) obtaining a weighted standardized uptake value ratio (weighted SUVR) for each divided region by using the standard value and the standardized uptake value ratio; and (d) generating dementia diagnosis assistance information indicating the possibility that the subject has dementia by applying the weighted standardized uptake value ratio of each divided region to a machine learning algorithm trained in advance.

Further, in the method in accordance with another preferred embodiment of the present invention, the step (a) may include: (a1) dividing the brain region included in a magnetic resonance imaging (MRI) image of the subject for diagnosis into a plurality of predefined divided regions and registering the image of the brain region with a positron emission tomography (PET) image of the subject for diagnosis; and (a2) calculating a standardized uptake value ratio (SUVR) for each of the divided regions in the registered image.

Further, in the method in accordance with another preferred embodiment of the present invention, the standard value may represent a degree of proximity of the standardized uptake value ratio to an average value of standardized uptake value ratios of a group of Alzheimer's patients and an average value of standardized uptake value ratios of a normal group.

Further, in the method in accordance with another preferred embodiment of the present invention, the standard interval may be defined by setting, as both ends of a regular interval, the average value of the standardized uptake value ratios of the group of the Alzheimer's patients and the average value of the standardized uptake value ratios of the normal group for a region corresponding to each of the plurality of divided regions.

Further, in the method in accordance with another preferred embodiment of the present invention, the standard interval may be an interval generated by transforming the average value of the standardized uptake value ratios of the normal group to correspond to 0 according to a predefined transformation formula, and transforming the average value of the standardized uptake value ratios of the group of the Alzheimer's patients to correspond to a predetermined number greater than 0 according to the transformation formula, and the standard value may be obtained by transforming the standardized uptake value ratio according to the transformation formula.

Further, in the method in accordance with another preferred embodiment of the present invention, the transformation formula may be defined as $$y = \frac{(x-B)}{(A-B)} \times 100,$$

where

A represents the average value of the standardized uptake value ratios of the group of the Alzheimer's patients, B represents the average value of the standardized uptake value ratios of the normal group, and x represents a parameter to be transformed.

Further, in the method in accordance with another preferred embodiment of the present invention, the step (c) may include obtaining a weighted standardized uptake value ratio (weighted SUVR) for each divided region by multiplying the standard value by the standardized uptake value ratio for each divided region.

In accordance with a preferred embodiment of the present invention in order to solve the aforementioned problems, disclosed is a computer program that is stored in a non-transitory storage medium and executed in a computer including a processor, the computer program performing the method for providing information needed for dementia diagnosis.

In accordance with a preferred embodiment of the present invention in order to solve the aforementioned problems, disclosed is an apparatus for providing information needed for dementia diagnosis, the apparatus including a processor and a memory for storing predetermined instructions, in which the processor is configured to, when executing the instructions stored in the memory, (a) calculate a standardized uptake value ratio (SUVR) for each of divided regions obtained by dividing a brain region of a brain image of a subject for diagnosis into a plurality of predefined divided regions; (b) obtain a standard value by mapping the standardized uptake value ratio of each divided region to a standard interval defined in advance for each divided region; (c) obtain a weighted standardized uptake value ratio (weighted SUVR) for each divided region by using the standard value and the standardized uptake value ratio; and (d) generate dementia diagnosis assistance information indicating the possibility that the subject has dementia by applying the weighted standardized uptake value ratio of each divided region to a machine learning algorithm trained in advance.

Further, in the apparatus in accordance with another preferred embodiment of the present invention, in the step (a), the processor is further configured to: (a1) divide the brain region included in a magnetic resonance imaging (MRI) image of the subject for diagnosis into a plurality of predefined divided regions and register the image of the brain region with a positron emission tomography (PET) image of the subject for diagnosis; and (a2) calculate a standardized uptake value ratio (SUVR) for each of the divided regions in the registered image.

Further, in the apparatus in accordance with another preferred embodiment of the present invention, the standard value may represent a degree of proximity of the standardized uptake value ratio to an average value of standardized uptake value ratios of a group of Alzheimer's patients and an average value of standardized uptake value ratios of a normal group.

Further, in the apparatus in accordance with another preferred embodiment of the present invention, the standard interval may be defined by setting, as both ends of a regular interval, the average value of the standardized uptake value ratios of the group of the Alzheimer's patients and the average value of the standardized uptake value ratios of the normal group for a region corresponding to each of the plurality of divided regions.

Further, in the apparatus in accordance with another preferred embodiment of the present invention, the standard interval may be an interval generated by transforming the average value of the standardized uptake value ratios of the normal group to correspond to 0 according to a predefined transformation formula, and transforming the average value of the standardized uptake value ratios of the group of the Alzheimer's patients to correspond to a predetermined number greater than 0 according to the transformation formula, and the standard value may be obtained by transforming the standardized uptake value ratio according to the transformation formula.

Further, in the apparatus in accordance with another preferred embodiment of the present invention, the transformation formula may be defined as $$y = \frac{(x-B)}{(A-B)} \times 100,$$

where

A represents the average value of the standardized uptake value ratios of the group of the Alzheimer's patients, B represents the average value of the standardized uptake value ratios of the normal group, and x represents a parameter to be transformed.

Further, in the apparatus in accordance with another preferred embodiment of the present invention, the processor is further configured to obtain a weighted standardized uptake value ratio (weighted SUVR) for each divided region by multiplying the standard value by the standardized uptake value ratio for each divided region.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIG. 2 is a table showing an example of Alzheimer's group data and normal group data that are stored in a memory of the present invention;

FIG. 4 is a diagram illustrating an example of an MRI brain image and a PET brain image that are input to an apparatus for providing information needed for dementia diagnosis;

FIG. 5 is a diagram illustrating an example of divided regions of a brain image in accordance with a preferred embodiment of the present invention;

DETAILED DESCRIPTION OF THE PREFERRED EMBODIMENTS

Figure 1:
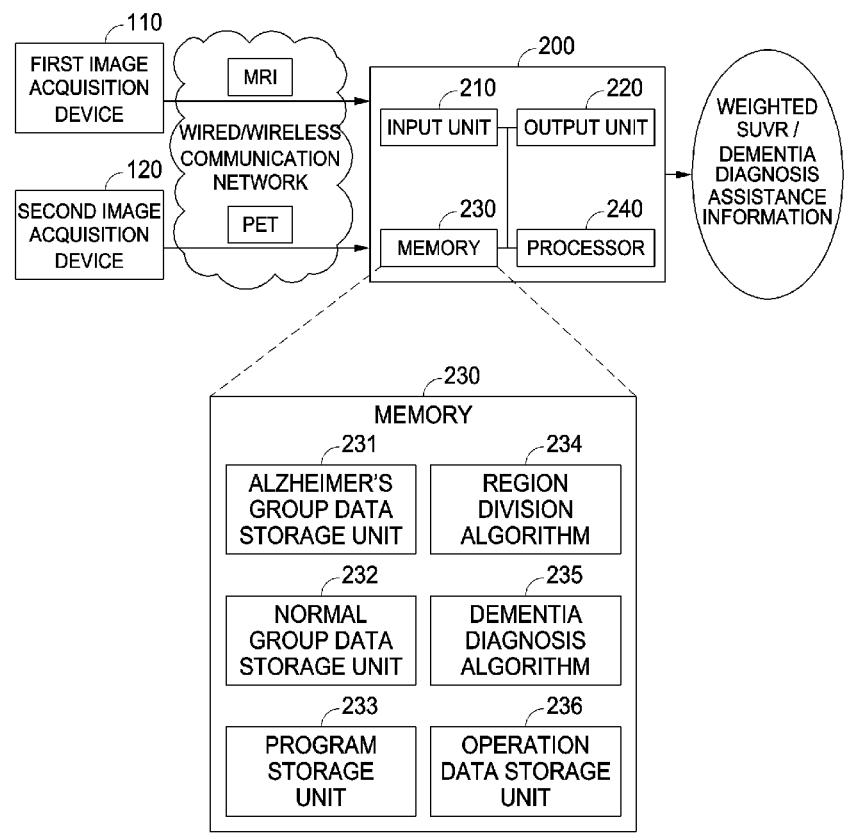
FIG. 1 is a diagram illustrating an apparatus for providing information needed for dementia diagnosis in accordance with a preferred embodiment of the present invention.

Hereinafter, preferred embodiments of the present invention will be described with reference to the drawings.

Here, the above-mentioned objects, features and advantages of the present invention will become more apparent through the following detailed description in conjunction with the accompanying drawings. However, it is to be understood that the present invention may be variously modified and embodied, and thus particular embodiments thereof will be illustrated in the drawings and described in detail.

Like reference numerals throughout the specification refer to like elements in principle. In addition, components having the same function within the scope of the same idea shown in the drawings of each embodiment will be described using the same reference numerals.

When a part "includes" an element, in the entire specification herein, unless described to the contrary, the term "includes" does not indicate that another element is excluded but instead indicates that the other element may be further included. In addition, the terms including "unit" and "module" described in the specification refer to units of performing at least one function or operation, which may be implemented by hardware or software, or by a combination of hardware and software.

When it is determined that the detailed description of the known technology or configuration related to the present invention may unnecessarily obscure the subject matter of the present invention, the detailed description thereof will be omitted. In addition, numbers (e.g., first, second, and the like) used in the description of the present specification are only identification symbols for distinguishing one component from other components.

FIG. 1 is a diagram illustrating an apparatus 200 for providing information needed for dementia diagnosis in accordance with a preferred embodiment of the present invention.

Referring to FIG. 1, the apparatus 200 for providing information needed for dementia diagnosis in accordance with an embodiment of the present invention is connected to a first image acquisition device 110 and a second image acquisition device 120 through a wired or wireless communication network, and receives an MRI image and a PET image from the first image acquisition device 110 and the second image acquisition device 120, respectively.

Here, the wired or wireless communication network may be implemented as any one of a mobile phone mobile communication network, a local area network (LAN), a wireless personal area network (WPAN), and a wireless local area network (WLAN), or may be implemented as a combination of two or more of them.

In a preferred embodiment of the present invention, the first image acquisition device 110 may be implemented as an MRI imaging device that outputs an MRI brain image by imaging a brain region of a subject for diagnosis, the second image acquisition device 120 may be implemented as a PET imaging device that outputs a PET brain image by imaging the brain region of a subject for diagnosis, and the apparatus 200 for providing information needed for dementia diagnosis may receive the MRI brain image and the PET brain image in real time at the same time as imaging.

In addition, the first image acquisition device 110 and the second image acquisition device 120 may capture the MRI brain image and the PET brain image and store the images therein, and when the apparatus 200 for providing information needed for dementia diagnosis requests the MRI brain image and PET brain image of the subject for diagnosis, the first image acquisition device 110 and the second image acquisition device 120 may provide the MRI brain image and PET brain image of the subject for diagnosis to the apparatus 200 for providing information needed for dementia diagnosis.

In addition, the first image acquisition device 110 and the second image acquisition device 120 may be implemented as a database server that stores MRI brain images and PET brain images of a plurality of subjects for diagnosis that have been generated in advance.

Here, the MRI brain image is preferably a T1 weighted MRI image, but is not limited thereto, and the PET brain image may be an amyloid PET image or a Tau PET image.

In addition, the apparatus 200 for providing information needed for dementia diagnosis in accordance with a preferred embodiment of the present invention includes a processor 240, a memory 230, an input unit 210, and an output unit 220.

Meanwhile, the memory 230 in accordance with a preferred embodiment of the present invention may store instructions executable by the processor 240 and programs executed by the processor 240, and store input/output data.

Examples of the memory 230 include a hard disk drive (HDD), a solid state drive (SSD), a flash memory, a read-only memory (ROM), a random access memory (RAM), and the like. The memory 230 may be replaced by operating a web storage or a cloud server performing a function of a storage medium on the Internet.

When the memory 230 of the present invention is conceptually partitioned according to the data stored therein, the memory 230 includes a program storage unit 233, an Alzheimer's group data storage unit 231, and a normal group data storage unit 232, a region division algorithm 234, a dementia diagnosis algorithm 235, and an operation data storage unit 236.

The program storage unit 233 stores a program including instructions for being loaded into the processor 240 and performing a method for providing information needed for dementia diagnosis, which will be described later with reference to FIG. 3.

The Alzheimer's group data storage unit 231 may store a registered image obtained by registering MRI brain images and PET brain images of members of the Alzheimer's group prepared in advance, and may store images obtained by dividing the registered image into a predefined number of regions and SUVR data generated for each of the divided regions. In addition, the Alzheimer's group data storage unit 231 may calculate the average value of the SUVRs of the corresponding region of all members of the group of the Alzheimer's patients for each of the divided brain regions and store the average value.

FIG. 2 is a table showing an example of Alzheimer's group data and normal group data that are stored in the memory 230 of the present invention.

As shown in FIG. 2, data for M members $A_1$ to $A_M$ are stored in the Alzheimer's group, and for each member, N SUVR values $V_{A1R1}$ to $V_{A1RN}, \ldots, V_{AMR1}$ to $V_{AMRN}$ for N regions $R_1$ to $R_N$ obtained by dividing a brain image region of the member are stored. In addition, for each region, average values $AV_{AR1}$ to $AV_{ARN}$ of SUVRs of the corresponding region for the respective members are stored. Accordingly, the Alzheimer's group data storage unit 231 stores N average values $AV_{AR1}$ to $AV_{ARN}$ of the SUVRs for each of N regions corresponding to the number of divided regions.

In a preferred embodiment of the present invention, the brain image region is divided into 97 regions according to a predefined brain map and the Alzheimer's group data storage unit 231 stores the average values of the SUVRs of each of the 97 regions; however, the number of regions is not limited to 97.

In addition, since only the average values of the SUVRs for each region are used in the dementia diagnosis assistance information generating process of the present invention, the Alzheimer's group data storage unit 231 may store only average values $AV_{AR1}$ to $AV_{ARN}$ of a predefined number of divided regions without storing the brain images of Alzheimer's members.

On the other hand, the normal group data storage unit 232 may use the same method as the Alzheimer's group data, as shown in FIG. 2 to store a registered image obtained by registering MRI brain images and PET brain images of members of the normal group and an image obtained by dividing the registered image into a predefined number of regions. In addition, the normal group data storage unit 232 may store SUVR values $V_{B1R1}$ to $V_{B1RN}, \ldots, V_{BMR1}$ to $V_{BMRN}$ calculated for each of the divided regions $R_1$ to $R_N$ of all normal members $B_1$ to $B_M$, and may store average values $AV_{BR1}$ to $AV_{BRN}$ of the SUVRs of the corresponding region of all members of the normal group for each divided brain region.

In a preferred embodiment of the present invention, as with the Alzheimer's group, for the normal group, the brain image region is divided into 97 regions according to a predefined brain map and the average values of the SUVRs of each of the 97 regions are stored; however, the number of divided regions is not limited to 97. In addition, the normal group data storage unit 232 may store only the average values $AV_{BR1}$ to $AV_{BRN}$ of the SUVRs of a predefined number of divided regions without storing brain images of normal members.

The region division algorithm 234 is trained by a deep learning method and stored as an algorithm trained to divide an MRI brain image into a predefined number of divided regions.

The dementia diagnosis algorithm 235 is trained by a machine learning method, and is stored as an algorithm trained to generate dementia diagnosis assistance information indicating the possibility that the subject has dementia using a weighted SUVR value for each region, which will be described later, when the weighted SUVR value is input.

To briefly explain an example of the dementia diagnosis algorithm 235 using machine learning of the present invention, first, a weighted SUVR for an Alzheimer's (AD) group is obtained, and a weighted SUVR for a normal group is obtained.

Then, according to the supervised learning method of the machine learning algorithm, the weighted SUVR of each group is set as the input of the machine learning algorithm as a feature value, and the corresponding result of the input, i.e., whether it corresponds to Alzheimer's disease (AD) (e.g., "1") or normal person recognition (e.g., "0") or the possibility that the subject has dementia is set as an output. In this case, general machine learning algorithms such as SVM, Random Forest, and Decision tree may be applied as machine learning algorithms.

When the learning is completed, when the weighted SUVR of the subject for diagnosis is input, the determination result (whether it is normal or AD, or the possibility that the subject has dementia) may be output through the learned machine learning algorithm.

Meanwhile, the input unit 210 of the apparatus 200 for providing information needed for dementia diagnosis may be implemented as a typical input means such as a mouse and a keyboard, and may receive setting information, selection information, or the like, from the user and output received information to the processor 240. In addition, the input unit 210 may include a communication module (not shown) therein to receive MRI brain images and PET brain images from the first image acquisition device 110 and the second image acquisition device 120 through a wired/wireless communication network and store the received images in the memory 230.

The output unit 220 may be implemented as a typical output means such as a monitor and a printer to display the data generated by the processor 240 to the user.

The processor 240 in accordance with a preferred embodiment of the present invention may be implemented as a central processing unit (CPU) or a similar device, and performs each step of the method for providing information needed for dementia diagnosis, which will be described later with reference to FIG. 3, by executing instructions stored in the memory 230.

Figure 3:
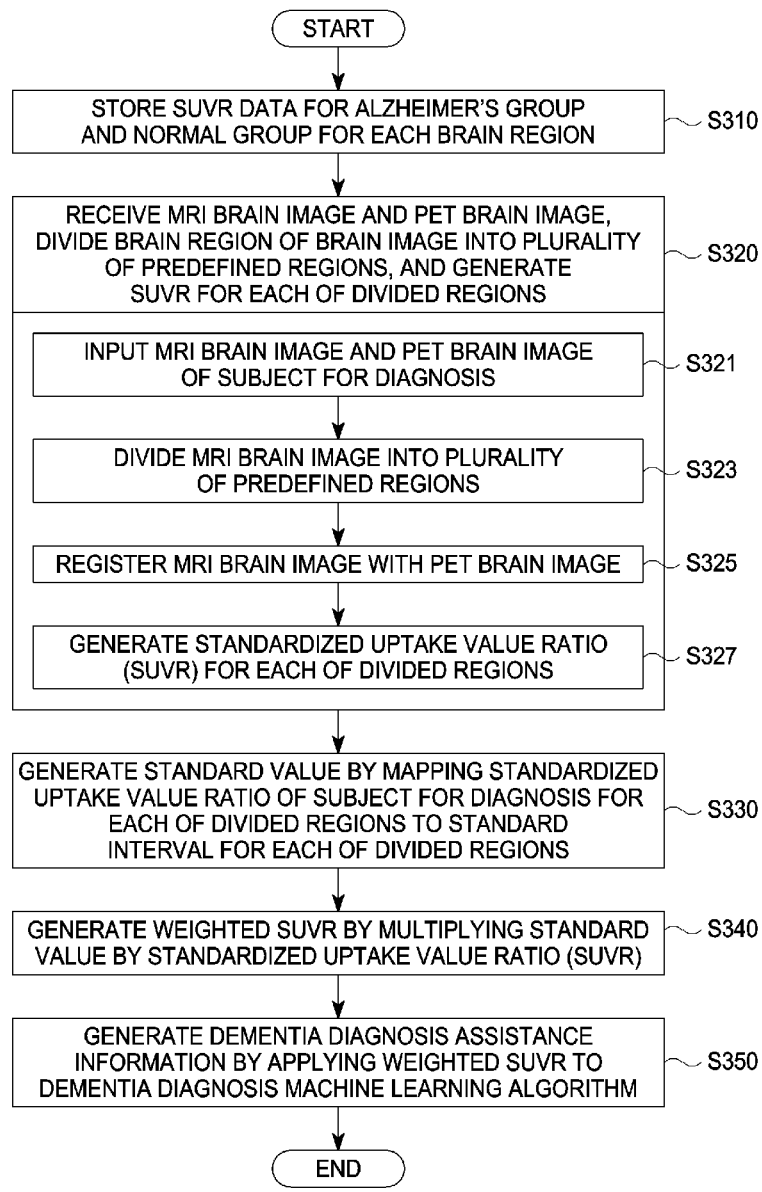
FIG. 3 is a flowchart illustrating a method for providing information needed for dementia diagnosis in accordance with a preferred embodiment of the present invention.

FIG. 3 is a flowchart illustrating a method for providing information needed for dementia diagnosis in accordance with a preferred embodiment of the present invention. With further reference to FIG. 3, a processing operation of the processor 240 of the present invention and a method for providing information needed for dementia diagnosis performed by the processor 240 in accordance with a preferred embodiment of the present invention will be described.

First, as described above, SUVR data for each of the brain regions of the Alzheimer's group and the normal group are stored in the memory 230 of the present invention (S310). An example of SUVR data for each of the brain regions of the Alzheimer's group and the normal group stored in the memory 230 is as described above with reference to FIG. 2.

Then, the processor 240 of the apparatus 200 for providing information needed for dementia diagnosis receives an MRI brain image and a PET brain image of a subject for diagnosis of dementia, divides the brain region of the brain image into a plurality of predefined regions, and generates the SUVR for each divided region (S320).

Describing step S320 in more detail, as shown in (a) and (b) of FIG. 4, the processor 240 receives the MRI brain image of the subject for diagnosis from the first image acquisition device 110, and receives the PET brain image of the subject for diagnosis from the second image acquisition device 120 (S321). In this case, the MRI brain image is preferably a T1-weighted MRI brain image, and the PET brain image may be an amyloid PET image or a tau PET image as needed.

The processor 240 divides the MRI brain image into a plurality of predefined regions (refer to FIG. 5) by using a deep learning-based region division algorithm stored in the memory 230 (S323). As described above, in the preferred embodiment of the present invention, the processor 240 divides the MRI brain image into 97 regions of interest according to the brain map; however, the division method and the number of divided regions are not limited thereto.

Figure 6:
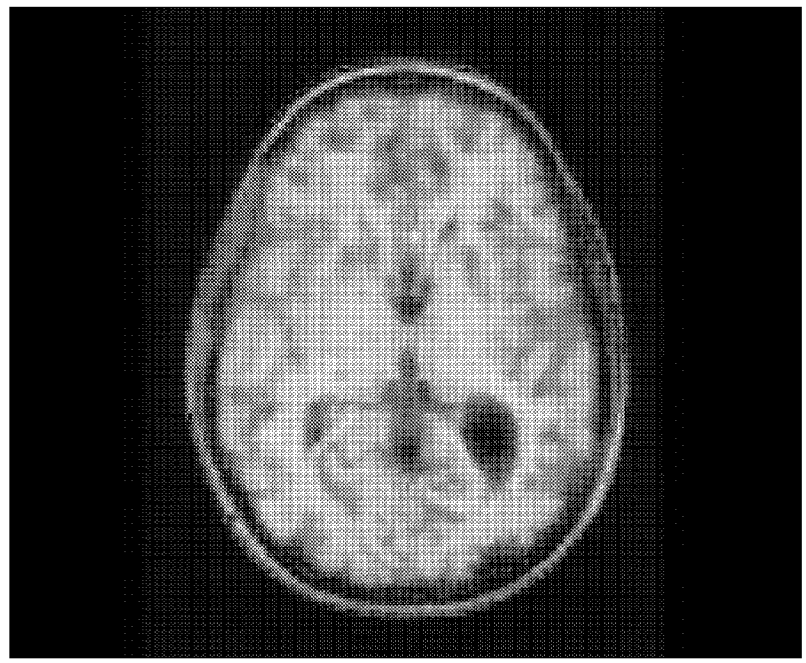
FIG. 6 is a diagram illustrating an example of a registered image in accordance with a preferred embodiment of the present invention.

Then, the processor 240 performs image registration on the MRI brain image and the PET brain image so that the two images are located in the same space through rigid transform (S325). FIG. 6 illustrates an example of an image in which an MRI brain image and a PET brain image are registered. As shown in FIG. 6, in the registered image, the processor 240 may identify regions corresponding to the divided regions in the PET brain image through the divided regions of the MRI brain image.

The processor 240 generates a standardized uptake value ratio (SUVR) for each divided region (S327).

The standardized uptake value ratio (SUVR) represents a ratio of amyloid (or tau) standardized uptake value (SUV) from two different regions within the same amyloid (or tau) image (target and reference region), and the amyloid (or tau) standardized uptake value (SUV) may represent the ratio of the concentration of radioactivity of the image to the concentration of radioactivity of the whole injected body. The method for obtaining the standardized uptake value ratio (SUVR) is a known technique in the technical field of the present invention, and thus a detailed description thereof will be omitted.

When the standardized uptake value ratio (SUVR) of the subject for diagnosis is obtained for each of the divided regions $R_1$ to $R_N$ in step S327, the respective standardized uptake value ratios $V_{SR1}$ to $V_{SRN}$ for the divided regions $R_1$ to $R_N$ are stored in the memory 230.

Next, the processor 240 generates a standard value by mapping the standardized uptake value ratio $V_{SR1}$ to $V_{SRN}$ of the subject for diagnosis for each of the divided regions to a standard interval for each of the divided regions (S330).

Here, the standard value represents a degree of proximity of the standardized uptake value ratio of the subject for diagnosis for each of divided regions to an average value of standardized uptake value ratios of a group of Alzheimer's patients and an average value of standardized uptake value ratios of a normal group.

In addition, the standard interval to which the standardized uptake value ratio of the subject for diagnosis for each of the divided regions is to be mapped is defined by setting, as both ends of a regular interval, the average value of the standardized uptake value ratios of the group of the Alzheimer's patients and the average value of the standardized uptake value ratios of the normal group for each of the plurality of divided regions.

In the preferred embodiment of the present invention, the standard interval is an interval generated by transforming the average value of the standardized uptake value ratios of the group of the Alzheimer's patients to correspond to 100 according to a predetermined transformation formula and transforming the average value of the standardized uptake value ratios of the normal group to correspond to 0 according to the transformation formula, and the standard value of the standardized uptake value ratio of the subject for diagnosis for each of the regions is a value obtained by transforming the standardized uptake value ratio according to the same transformation formula. In this case, the transformation formula may be defined as in Equation 1 below.

$$y = \frac{(x-B)}{(A-B)} \times 100 \quad \text{[Equation 1]}$$

In the Equation 1, A represents the average value of the standardized uptake value ratios of the group of the Alzheimer's patients, B represents the average value of the standardized uptake value ratios of the normal group, and x represents the SUVR of the subject for diagnosis, which is a parameter to be transformed.

Figure 7:
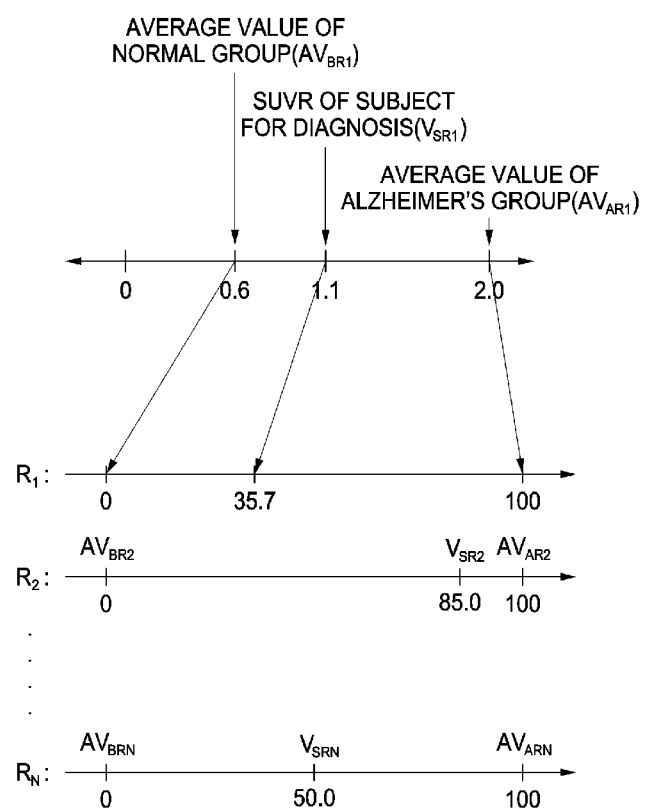
FIG. 7 is a diagram for describing a standard interval obtained from average values of standardized uptake value ratios of a group of Alzheimer's patients and a normal group for each region in accordance with a preferred embodiment of the present invention, and a standard value of a subject for diagnosis mapped for each region accordingly.

FIG. 7 is a diagram for describing a standard interval obtained from average values of standardized uptake value ratios of a group of Alzheimer's patients and a normal group for each region in accordance with a preferred embodiment of the present invention, and a standard value of a subject for diagnosis mapped for each region accordingly.

Referring to FIG. 7, assuming that the average value $AV_{AR1}$ of the group of Alzheimer's patients in a first divided region $R_1$ is 2.0, the average value $AV_{BR1}$ of the normal group is 0.6, and the SUVR of the subject for diagnosis is 1.1, in the standard interval of the divided region $R_1$, the average value $AV_{BR1}$ of the normal group of 0.6 corresponds to 0, the average value $AV_{AR1}$ of the group of Alzheimer's patients of 2.0 corresponds to 100, and the SUVR of the subject for diagnosis of 1.1 corresponds to 35.7 according to Equation 1 above.

In the above example, the SUVR of the divided region R1 of the subject for diagnosis is 1.1, which is at a borderline for determining whether PET is positive and negative, but when transformed to a standard interval, the standard value does not exceed 50, which is closer to the normal group, which makes it possible to provide useful information in determining whether PET is positive and negative.

In the same manner, the processor 240 generates a standard interval by transforming the average value of the normal group to 0 for each of the remaining divided regions $R_2$ to $R_N$ and transforming the average value of the group of Alzheimer's patients to 100, and generates a standard value to be mapped to the standard interval by transforming the SUVR of the subject for diagnosis of dementia in the same way.

Then, the processor 240 generates a weighted SUVR by multiplying the standard value of the subject for diagnosis by the standardized uptake value ratio (SUVR) generated in step S327 for each region (S340).

The weighted SUVR is a numerically comprehensive expression of the SUVR obtained for each of the regions and which of the average value of the SUVRs of the group of Alzheimer's subjects and the average value of the SUVRs of the normal group the SUVR of the corresponding region is closer to, thereby providing more useful information in the dementia diagnosis.

Meanwhile, the processor 240 generates and outputs to medical staff a dementia diagnosis assistance information indicating the possibility that the subject has dementia by applying the weighted SUVR obtained for each of the regions to a previously trained dementia diagnosis machine learning algorithm (S350).

In step S350, the processor 240 outputs the SUVR, the weighted SUVR, and the dementia diagnosis assistance information for each of the regions together, thereby providing various information to be used for diagnosis to a user (medical staff) performing dementia diagnosis.

Meanwhile, in the above example, the standard interval was set to 0 to 100, but according to another embodiment, by modifying Equation 1 above to transform the average value of the SUVRs of the Alzheimer's group to 1, the standard interval may be set to 0 to 1.

Figure 8:
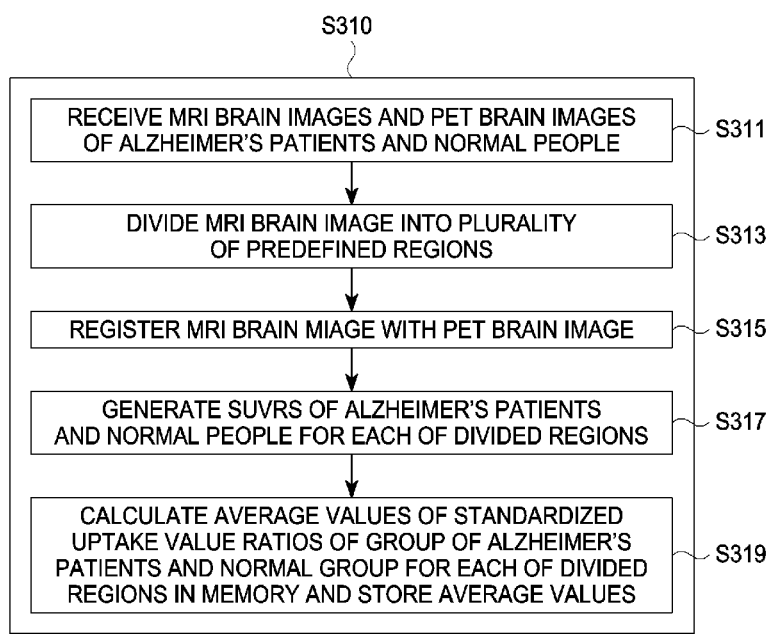
FIG. 8 is a flowchart for describing a process of obtaining average values of SUVRs of an Alzheimer's group and a normal group for each divided region and storing the average values in a memory in accordance with a preferred embodiment of the present invention.

FIG. 8 is a flowchart for describing a process of obtaining average values of the SUVRs of an Alzheimer's group and a normal group for each of the divided regions and storing the average values of the SUVRs in the memory 230 in accordance with a preferred embodiment of the present invention.

The process of calculating the average values of the SUVRs of the Alzheimer's group and the normal group for each of the divided regions is the same as the above-described step S320, except that the subjects are members of the group of Alzheimer's patients and members of the normal group.

Accordingly, briefly describing only the overall flow with reference to FIG. 8, the processor 240 receives MRI brain images of Alzheimer's patients and normal people from the first image acquisition device 110, and receives PET brain images of Alzheimer's patients and normal people from the second image acquisition device 120 (S311). In this case, the MRI brain image is preferably a T1-weighted MRI brain image, and the PET brain image may be an amyloid PET image or a tau PET image as needed.

As shown in FIG. 5, the processor 240 divides the MRI brain image into a plurality of predefined regions by using a deep learning-based region division algorithm stored in the memory 230 (S313). As described above, in the preferred embodiment of the present invention, the processor 240 divides the MRI brain image into 97 regions of interest according to the brain map; however, the division method and the number of divided regions are not limited thereto.

Then, the processor 240 performs image registration on the MRI brain image and the PET brain image so that the two images are located in the same space through rigid transform (S315).

The processor 240 generates standardized uptake value ratios (SUVR) of the Alzheimer's patients and normal people for each divided region (S317).

Then, the processor 240 calculates the average values $AV_{AR1}$ to $AV_{ARN}$ and $AV_{BR1}$ to $AV_{BRN}$ of the standardized uptake value ratios of the group of Alzheimer's patients and the normal group for each of the divided regions $R_1$ to $R_N$ in the memory 230 and stores the average values (S319).

The method for providing information needed dementia diagnosis in accordance with a preferred embodiment of the present invention described above may be implemented as a computer program stored in a non-transitory storage medium by being implemented as computer-executable instructions.

In the apparatus and method for providing information needed for dementia diagnosis in accordance with preferred embodiments of the present invention, an MRI brain image and a PET brain image of a subject for diagnosis are received, the MRI brain image is divided into a plurality of regions, and then the MRI brain image is registered with the PET brain image. Then, a standardized uptake value ratio of each divided region is obtained from the registered image, and for each divided region, a standard value indicating the degree of proximity of a standardized uptake value ratio of the subject for diagnosis to the average value of the standardized uptake value ratios of the group of the Alzheimer's patients and the average value of the standardized uptake value ratios of the normal group, which are stored in advance, is obtained. Then, for each divided region, a weighted standardized uptake value ratio obtained by multiplying the standardized uptake value ratio of the subject for diagnosis by the standard value is provided, and a machine learning algorithm trained in advance is applied to generate dementia diagnosis assistance information indicating the possibility that the subject has dementia, and thus, it is possible to provide various information needed for dementia diagnosis and improve the accuracy of dementia diagnosis as compared to the related art that has provided simply the standardized uptake value ratio of absolute values.

The storage medium includes all kinds of recording devices in which data that may be read by a computer system is stored. Examples of computer-readable storage media include read only memory (ROM), random access memory (RAM), compact disc ROMs (CD-ROM), magnetic tapes, floppy disks, and optical data storage devices. In addition, the computer-readable storage medium may be distributed in a computer system connected through a network, so that the computer-readable code may be stored and executed in a distributed manner.

As described above, the present invention has been shown and described with reference to preferred embodiments thereof. It will be understood by those skilled in the art that various modifications in form may be made therein without departing from the spirit and scope of the invention as defined by the appended claims. Therefore, the disclosed embodiments should be considered in an illustrative sense and not for purposes of limitation. The scope of the invention is defined not by the detailed description of the invention but by the appended claims, and all differences within the scope will be construed as being included in the invention.

What is claimed is:

1. A method for providing information needed for dementia diagnosis that is performed in an apparatus for providing information needed for dementia diagnosis, the apparatus including a processor and a memory for storing predetermined instructions, the method comprising:

(a) calculating a standardized uptake value ratio (SUVR) for each of regions (divided regions) obtained by dividing a brain region of a brain image of a subject for diagnosis into a plurality of predefined regions;

(b) obtaining a standard value by mapping the standardized uptake value ratio of each divided region to a standard interval defined in advance for each divided region;

(c) obtaining a weighted standardized uptake value ratio (weighted SUVR) for each divided region by using the standard value and the standardized uptake value ratio; and (d) generating dementia diagnosis assistance information indicating the possibility that the subject has dementia by applying the weighted standardized uptake value ratio of each divided region to a machine learning algorithm trained in advance, wherein the standard interval is defined by setting, as both ends of a regular interval, the average value of the standardized uptake value ratios of the group of the Alzheimer's patients and the average value of the standardized uptake value ratios of the normal group for a region corresponding to each of the plurality of divided regions, and wherein the step (c) comprises obtaining a weighted standardized uptake value ratio (weighted SUVR) for each divided region by multiplying the standard value by the standardized uptake value ratio for each divided region.

2. The method of claim 1, wherein the step (a) comprises:

a step (a1) of dividing the brain region included in a magnetic resonance imaging (MRI) image of the subject for diagnosis into a plurality of predefined divided regions and registering the image of the brain region with a positron emission tomography (PET) image of the subject for diagnosis; and a step (a2) of calculating a standardized uptake value ratio (SUVR) for each of the divided regions in the registered image.

3. The method of claim 1, wherein the standard value represents a degree of proximity of the standardized uptake value ratio to an average value of standardized uptake value ratios of a group of Alzheimer's patients and an average value of standardized uptake value ratios of a normal group.

4. The method of claim 1, wherein the standard interval is an interval generated by transforming the average value of the standardized uptake value ratios of the normal group to correspond to 0 according to a predefined transformation formula, and transforming the average value of the standardized uptake value ratios of the group of the Alzheimer's patients to correspond to a predetermined number greater than 0 according to the transformation formula, and the standard value is obtained by transforming the standardized uptake value ratio according to the transformation formula.

5. The method of claim 4, wherein the transformation formula is defined as $$y = \frac{(x-B)}{(A-B)} \times 100,$$

where A represents the average value of the standardized uptake value ratios of the group of the Alzheimer's patients, B represents the average value of the standardized uptake value ratios of the normal group, and x represents a parameter to be transformed.

6. A non-transitory computer readable storage medium, storing a computer program executed in a computer including a processor to perform the method for providing information needed for dementia diagnosis of claim 1.

7. An apparatus for providing information needed for dementia diagnosis, the apparatus comprising:

a processor; and a memory for storing predetermined instructions, wherein the processor is configured to, when executing the instructions stored in the memory, (a) calculate a standardized uptake value ratio (SUVR) for each of divided regions obtained by dividing a brain region of a brain image of a subject for diagnosis into a plurality of predefined divided regions;

(b) obtain a standard value by mapping the standardized uptake value ratio of each divided region to a standard interval defined in advance for each divided region;

(c) obtain a weighted standardized uptake value ratio (weighted SUVR) for each divided region by using the standard value and the standardized uptake value ratio; and (d) generate dementia diagnosis assistance information indicating the possibility that the subject has dementia by applying the weighted standardized uptake value ratio of each divided region to a machine learning algorithm trained in advance, wherein the standard interval is defined by setting, as both ends of a regular interval, the average value of the standardized uptake value ratios of the group of the Alzheimer's patients and the average value of the standardized uptake value ratios of the normal group for a region corresponding to each of the plurality of divided regions, and wherein the processor is further configured to obtain a weighted standardized uptake value ratio (weighted SUVR) for each divided region by multiplying the standard value by the standardized uptake value ratio for each divided region in the step (c).

8. The apparatus of claim 7, wherein the processor is further configured to:

(a1) divide the brain region included in a magnetic resonance imaging (MRI) image of the subject for diagnosis into a plurality of predefined divided regions and register the image of the brain region with a positron emission tomography (PET) image of the subject for diagnosis; and (a2) calculate a standardized uptake value ratio (SUVR) for each of the divided regions in the registered image.

9. The apparatus of claim 7, wherein the standard value represents a degree of proximity of the standardized uptake value ratio to an average value of standardized uptake value ratios of a group of Alzheimer's patients and an average value of standardized uptake value ratios of a normal group.

10. The apparatus of claim 7, wherein the standard interval is an interval generated by transforming the average value of the standardized uptake value ratios of the normal group to correspond to 0 according to a predefined transformation formula, and transforming the average value of the standardized uptake value ratios of the group of the Alzheimer's patients to correspond to a predetermined number greater than 0 according to the transformation formula, and the standard value is obtained by transforming the standardized uptake value ratio according to the transformation formula.

11. The apparatus of claim 10, wherein the transformation formula is defined as $$y = \frac{(x-B)}{(A-B)} \times 100,$$

where A represents the average value of the standardized uptake value ratios of the group of the Alzheimer's patients, B represents the average value of the standardized uptake value ratios of the normal group, and x represents a parameter to be transformed.

* * * * *